United States Patent
Rey et al.

(10) Patent No.: US 7,662,997 B2
(45) Date of Patent: Feb. 16, 2010

(54) SYNTHESIS AND APPLICATIONS OF 2-OXO-4-METHYLTHIOBUTYRIC ACID, ITS SALTS AND ITS DERIVATIVES

(75) Inventors: Patrick Rey, Lyon (FR); Gilbert Blanchard, Lagny le Sec (FR)

(73) Assignee: Adisseo Ireland Limited, Dublin (IE)

( * ) Notice: Subject to any disclaimer, the term of this patent is extended or adjusted under 35 U.S.C. 154(b) by 105 days.

(21) Appl. No.: 11/792,586

(22) PCT Filed: Dec. 29, 2005

(86) PCT No.: PCT/FR2005/003300

§ 371 (c)(1),
(2), (4) Date: Nov. 26, 2007

(87) PCT Pub. No.: WO2006/072711

PCT Pub. Date: Jul. 13, 2006

(65) Prior Publication Data

US 2008/0069920 A1 Mar. 20, 2008

(30) Foreign Application Priority Data

Dec. 30, 2004 (FR) .................................. 04 14084

(51) Int. Cl.
*C07C 323/52* (2006.01)
*C07C 323/60* (2006.01)
*C07C 319/18* (2006.01)
*C07C 319/20* (2006.01)

(52) U.S. Cl. ...................................... 562/577; 562/538

(58) Field of Classification Search ........................ None
See application file for complete search history.

(56) References Cited

U.S. PATENT DOCUMENTS

| 5,081,096 A | 1/1992 | Monnier et al. |
| 5,138,077 A | 8/1992 | Monnier et al. |
| 2005/0239888 A1 | 10/2005 | Franzone et al. |

FOREIGN PATENT DOCUMENTS

| FR | 2 317 919 | 2/1977 |
| WO | WO 91/15471 | 10/1991 |
| WO | WO 00/24702 | 5/2000 |
| WO | WO 2004/012706 A1 | 2/2004 |

OTHER PUBLICATIONS

Pinxt et al. Applied Cataltsis A: General, 2000, 191, pp. 45-54.*
Du et al., "Snake venom L-amino acid Oxidases," 40 *Toxicon* 659 (2002).
Schummer et al., "Polyfunctional®-2-Hydroxycarboxylic Acids by Reduction of 2-Oxo Acids with Hydrogen Gas or Formate and Resting Cells of *Proteus vulgaris*," 47 *Tetrahedron* 9019 (1991).
Szwajcer et al., "Production of α-keto acids: 2. Immobilized whole cells of *Providencia* sp. PCM 1298 containing L-amino acid oxidase," 4 *Enzyme Microb. Technol.* 409 (1982).
Nam et al., "Synthesis of Deterium Labeled Plant Ethylene Precursor," 36 *Journal of Labelled Compounds and Radiopharmaceuticals* 431 (1994).
Kuwajima et al., "Quaternary Ammonium Fluoride-Catalyzed Conjugate Addition of Thiols to C=C Double Bonds," *Synthesis* 602 (1976).
Nicolet, "The Addition of Mercaptans to Certain Double Bonds," 57 *Journal of the American Chemical Society* 1098 (1935).
Scislowski et al., "Methionine transamination—metabolic function and subcellular compartmentation," 129 *Molecular and Cellular Biochemistry* 39 (1993).

* cited by examiner

*Primary Examiner*—Daniel M Sullivan
*Assistant Examiner*—Yevegeny Valenrod
(74) *Attorney, Agent, or Firm*—Oliff & Berridge, PLC

(57) ABSTRACT

The invention relates to a process for preparing 2-oxo-4-methylthiobutyric acid (I), its salts and its derivatives

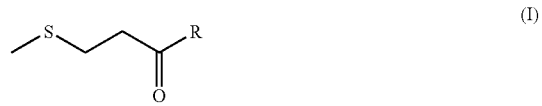

in which R represents a group chosen from COOH, COOR', $NH_2$, NHR' or NR'R", where R' and R" are chosen, independently of one another, from the group of linear or branched alkyl radicals having from 1 to 12 carbon atoms and cycloalkyl radicals having from 3 to 12 carbon atoms,
according to which process but-3-ene-1,2-diol (II) is catalytically and selectively oxidized to give 2-oxobut-3-enoic acid (III) and methyl mercaptan is selectively condensed with 2-oxobut-3-enoic acid (III).
2-Oxo-4-methylthiobutyric acid (I), its salts and its derivatives are used as food supplement, in particular in animal nutrition.

20 Claims, 1 Drawing Sheet

FIGURE
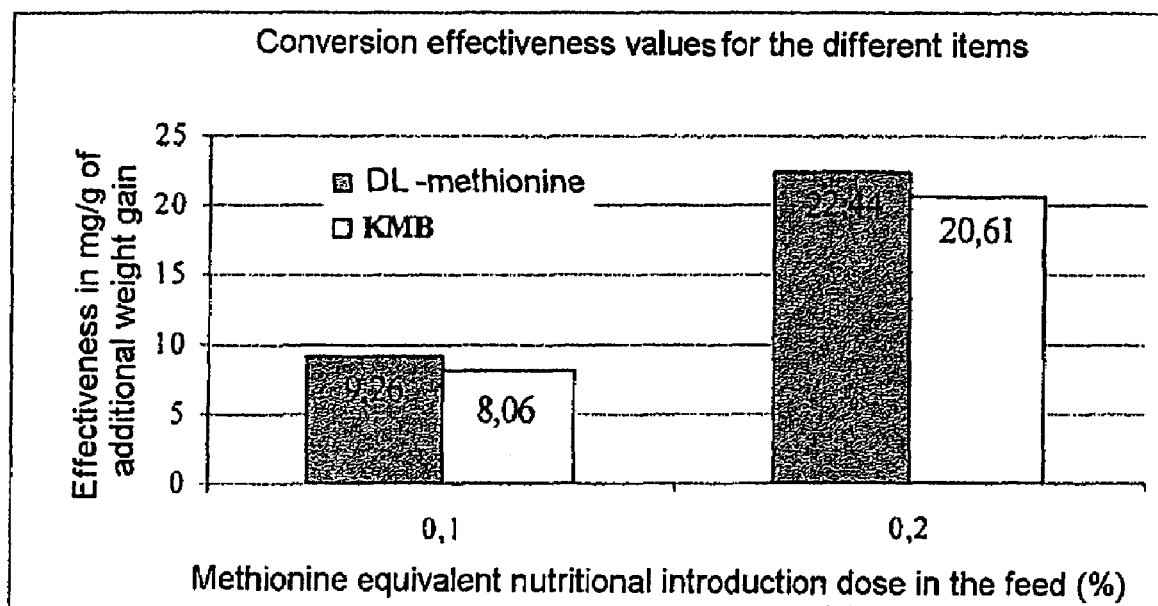

SYNTHESIS AND APPLICATIONS OF 2-OXO-4-METHYLTHIOBUTYRIC ACID, ITS SALTS AND ITS DERIVATIVES

The invention relates to the preparation of 2-oxo-4-methylthiobutyric acid (hereinafter denoted KMB), of its salts and of its derivatives and to their uses, in particular in animal nutrition.

Methionine is an essential sulphur-comprising amino acid which is involved in numerous metabolic processes, including mainly:

protein synthesis: methionine is not only a component of proteins, in the same way as the other amino acids, but also the amino acid which initiates the process of protein synthesis, which renders it all the more essential;

lipid metabolism: methionine is involved in the synthesis of the constituents of serum lipoproteins and it consequently plays a role in the transportation of lipids in the blood, their use and their deposition in the tissues.

For poultry, methionine is an essential amino acid and has to be added to the feed.

For dairy cows, it is a limiting amino acid with regard to milk production. In addition, methionine is favourably involved in the fertility and the hepatic function of cows.

Sufficient milk production and more generally a better general condition of cows are thus conditioned by an appropriate methionine diet. Milk production can even be increased by increasing the methionine content in the diet.

However, the free form of methionine is rapidly decomposed by the bacterial flora in the rumen of cows and only a very small fraction of the methionine joins the blood circulation.

Solutions have been devised to overcome this disadvantage by substituting, for methionine, a protected methionine, protected chemically or by coating, or a modified methionine, which exhibits an advantageous bioavailability of methionine in the blood. Thus, a protected methionine, Smartamine®, manufactured and sold by the Applicant Company, and two methionine analogues, 2-hydroxy-4-methylthiobutyric acid (HMB) and the isopropyl ester of HMB, which are not affected to any great extent by decomposition in the rumen, are known in particular.

The authors of the present invention have discovered that 2-oxo-4-methylthiobutyric acid (KMB) constitutes an advantageous analogue for substitution of methionine by exhibiting a high methionine bioavailability, the said analogue being capable of being obtained by a simple synthetic route which can be carried out on the industrial scale.

According to K. Mosbach et al., Enzyme and Microbial Technology, (1982) 4, No. 6, 409-413, and K. J. Clemetson et al., Toxicon, (2002) 40, 659-665, 2-oxo-4-methylthiobutyric acid is prepared on the laboratory scale by an enzymatic synthetic route. This synthesis cannot, however, be adapted to the industrial production of the said acid due to the disadvantages inherent in fermentation processes, such as the complexity of the infrastructures necessary for their implementation, the risk of microbiological contamination, the long reaction times and the losses in yield attributable to the enantioselectivity of the microorganism selected (H. Simon et al., Tetrahedron, (1990) 47, No. 43, 9019-9034).

H. Rapoport, J. Label. Compds. Radiopharm. (1994) Vol. 36, No. 5, p. 431-437, describes the synthesis of 2-oxo-4-methylthiobutyric acid in six stages from ethyloxylyl chloride. In this synthesis, methyl mercaptan is added to ethyl 4-chloro-3-oxo-3-butenoate, before or after its hydrogenation.

The authors have developed a process for the preparation of the abovementioned acid in two stages and under specific conditions which makes it possible to limit the reaction times and, in addition, to improve the reaction selectivity.

Thus, a first subject-matter of the invention is a process for preparing 2-oxo-4-methylthiobutyric acid, corresponding to the following formula (I):

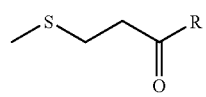

in which R represents a carboxyl group, and its salts, the said process comprising the following stages:

but-3-ene-1,2-diol (II) is catalytically and selectively oxidized to give 2-oxobut-3-enoic acid (III), according to the following reaction scheme (i):

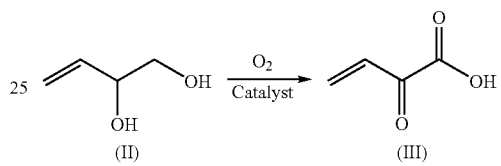

and methyl mercaptan is selectively condensed with 2-oxobut-3-enoic acid (III), according to the following reaction scheme (ii):

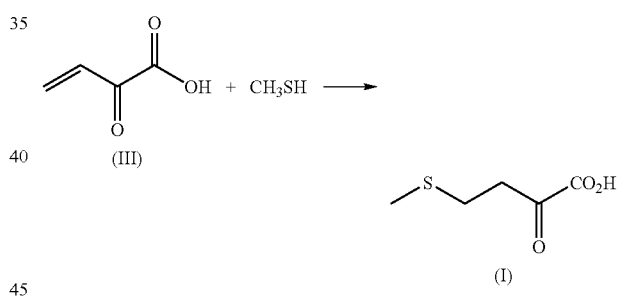

This process also makes it possible to prepare derivatives of 2-oxo-4-methylthiobutyric acid and the salts of these derivatives, the said derivatives corresponding to the following formula (I):

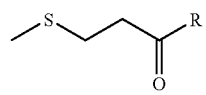

in which R represents a group chosen from COOR', CONH$_2$, CONHR' or CONR'R", where R' and R" are chosen, independently of one another, from the group of linear alkyl radicals, such as, for example, the methyl, ethyl, n-propyl, n-butyl and n-pentyl radicals, branched alkyl radicals, such as, for example, the isopropyl, isobutyl, sec-butyl, tert-butyl, isopentyl and isohexyl radicals, the said alkyl radicals having from 1 to 12 carbon atoms, and cycloalkyl radicals having from 3 to 12 carbon atoms, according to which process the preparation of 2-oxo-4-methylthiobutyric acid (I) above is supplemented by an esterification or amidation stage, that those skilled in the art can carry out based on their general knowledge.

According to the invention, the term "salts of 2-oxo-4-methylthiobutyric acid and of its derivatives" is understood to mean the salts such as those of calcium, sodium, magnesium, manganese or zinc.

Preferred alternative forms and implementations of the process of the invention are set out below and, in the context of the present invention, their characteristics can be considered alone or in combination.

For the stage of catalytic oxidation of but-3-ene-1,2-diol (II) to give 2-oxobut-3-enoic acid (III), the catalyst advantageously corresponds to the following characteristics:

The said catalyst comprises at least one noble metal chosen from palladium, platinum, ruthenium, iridium, rhodium and their mixtures.

The catalyst based on noble metals comprises at least one promoter chosen from bismuth, lead, antimony, tin, niobium, tellurium, indium, gallium, zinc, copper, nickel, cobalt, gold, silver, tungsten, molybdenum, rhenium, vanadium, chromium, manganese, iron and their mixtures.

The content of the noble metal or metals is between 0.1 and 10% by weight with respect to the catalytic support and preferably between 0.5 and 5% by weight.

The catalyst also comprises an inert support chosen from alumina, silica, active charcoals, graphite, titanium oxide, zirconia, silicon carbide, mixed oxides based on zirconium and on cerium, or acetylene black.

The content of promoter is between 0.005 and 500%, preferably between 0.005 and 100%, by weight of the weight of the noble metal or metals, and/or it can reach 100% by weight of the weight of the catalyst. The deposition of the promoter on the catalyst based on noble metals is advantageously carried out by impregnation of this promoter on the catalytic support.

A preferred catalyst comprises a noble metal chosen from palladium, platinum and their mixtures, a promoter chosen from bismuth, lead and their mixtures, and a support chosen from active charcoal and graphite.

The conditions of the oxidation reaction are advantageously as follows: it is carried out in an alkaline or neutral medium, at a pH maintained between 4 and 11, preferably between 5.5 and 7.5. To this end, an alkaline agent chosen from calcium hydroxide, sodium hydroxide, potassium hydroxide, lithium hydroxide, magnesium hydroxide, ammonia, sodium carbonate, zinc carbonate, manganese carbonate and their mixtures is added. The reaction is carried out at a temperature of between 10 and 95° C., preferably between 20 and 95° C., and better still between 25 and 70° C.; the duration of the oxidation is generally between 20 minutes and 15 hours.

The oxidation stage can be initiated by starting to flush with a gas mixture comprising oxygen, for example air.

The conditions for the condensation reaction of methyl mercaptan with 2-oxobut-3-enoic acid are advantageously as follows: methyl mercaptan is used in the gaseous form or in the liquid form; the reaction is carried out in the presence of a basic catalyst. The catalyst is chosen from aliphatic amines, such as methylamine, ethylamine, propylamine, butylamine, pentylamine, hexylamine, heptylamine and octylamine, aromatic amines, such as aniline or pyridine, hexamethylenetetramine, triethylamine, diisopropylethylamine, diazabicylo [2.2.2]octane, N,N-dimethylbenzylamine, N-methyldiphenylamine, N-ethyl-3,3'-diphenyldipropylamine or an N-alkylmorpholine, such as N-methylmorpholine, or triton B. These organic amines being optionally, indeed even advantageously, combined with an organic or inorganic acid; the organic acid is preferably chosen from formic acid, acetic acid, propanoic acid and butanoic acid, and the inorganic acid is advantageously chosen from phosphoric acid and sulphuric acid.

Another subject-matter of the invention is the process for preparing 2-oxobut-3-enoic acid (III) and its salts, in particular as intermediate compound in the synthesis of 2-oxo-4-methylthiobutyric acid, according to which but-3-ene-1,2-diol (II) is catalytically and selectively oxidized according to the reaction scheme (i) under any one of the abovementioned conditions, considered alone or in combination.

As stated above, 2-oxo-4-methylthiobutyric acid and its salts constitute methionine analogues which have a high bioavailability in cows and poultry. Thus, yet another subject-matter of the invention is a food supplement consisting of a compound and/or its salts, the said compound corresponding to the following formula (I):

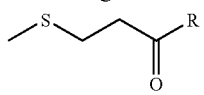

in which R represents a group chosen from COOR', CONH$_2$, CONHR' or CONR'R", where R' and R" are chosen, independently of one another, from the group of linear alkyl radicals, such as, for example, the methyl, ethyl, n-propyl, n-butyl and n-pentyl radicals, branched alkyl radicals, such as, for example, the isopropyl, isobutyl, sec-butyl, tert-butyl, isopentyl and isohexyl radicals, the said alkyl radicals having from 1 to 12 carbon atoms, and cycloalkyl radicals having from 3 to 12 carbon atoms. Preferably, the supplement of the invention consists of 2-oxo-4-methylthiobutyric acid (I) and/or its salts.

The invention also relates to a food ration comprising a cereals part, a concentrated feed part and a supplement of the invention as defined above.

Other subject-matters of the invention are a process for the administration of bioavailable methionine to a cow, comprising the administration to the cow of an above supplement, and the use, as food supplement for animal nutrition, of a compound and/or of its salts, the said compound corresponding to the formula (I)

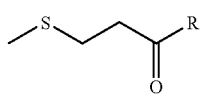

in which R represents a group chosen from COOR', CONH$_2$, CONHR' or CONR'R", where R' and R" are chosen, independently of one another, from the group of linear alkyl radicals, such as, for example, the methyl, ethyl, n-propyl, n-butyl and n-pentyl radicals, branched alkyl radicals, such as, for example, the isopropyl, isobutyl, sec-butyl, tert-butyl, isopentyl and isohexyl radicals, the said alkyl radicals having from 1 to 12 carbon atoms, and cycloalkyl radicals having from 3 to 12 carbon atoms.

The present invention is set out below in more detail and is then illustrated from examples demonstrating its advantages.

1) Oxidation Stage (i):

1.a) Preparation of but-3-ene-1,2-diol (II):

The diol (II) can be obtained from butadiene (IV) by mono-epoxidation of the latter to give 3,4-epoxy-1-butene (V), which is converted to the diol (II) by chemical opening of the epoxide functional group.

This preparation is illustrated by the reaction schemes (iii) and (iv) below:

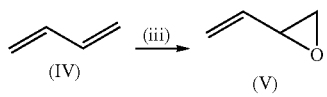

The monoepoxidation reaction is carried out by heterogeneous catalysis from supported silver-based catalysts activated by a promoter chosen from alkali metals, such as potassium, caesium and rubidium, as disclosed, for example, in the document U.S. Pat. No. 5,081,096, or activated by thallium, as disclosed in the document U.S. Pat. No. 5,138,077. These catalysts are prepared by conventional methods, such as impregnation and coprecipitation.

The selectivity of this reaction for 3,4-epoxy-1-butene (V) under the above conditions can exceed 95% and the conversion yield for (iii) oscillates between 12 and 15%. At the industrial stage, unconverted butadiene (IV) can be at least partially recycled.

The chemical opening of the epoxide functional group illustrated below is carried out conventionally in an aqueous medium:

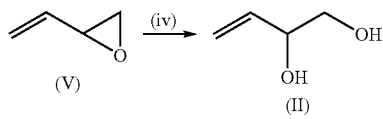

This opening is advantageously acid-catalysed, in the presence, for example, of acidic resins, under conditions disclosed in particular in the documents WO-A-91/15471 or WO-A-00/24702.

1.b) Oxidation of but-3-ene-1,2-diol (II):

The diol (II) can be provided in a liquid form, in the purified or unpurified state, or else in a crude aqueous solution form, that is to say of reduced purity, for example resulting from the above stage 1.a).

Whatever its form, the diol can be used directly for the catalytic oxidation reaction to give the α-keto acid (III). Advantageously, the aqueous solution which results from the opening of the epoxide (V) will be used directly in the stage for oxidation of the diol (II).

The catalyst for oxidation of the diol (II) comprises at least one noble metal chosen from palladium, platinum, ruthenium, iridium, rhodium and their mixtures. The content of the noble metal or metals is between 0.1 and 10% by weight with respect to the catalytic support and preferably between 0.5 and 5% by weight.

The catalytic support is chosen from alumina, silica, active charcoals, graphite, titanium oxide, zirconia, silicon carbide, mixed oxides based on zirconium and on cerium, or acetylene black.

The catalyst for oxidation of the diol (II) based on noble metals comprises at least one promoter chosen from bismuth, lead, antimony, tin, niobium, tellurium, indium, gallium, zinc, copper, nickel, cobalt, gold, silver, tungsten, molybdenum, rhenium, vanadium, chromium, manganese, iron and their mixtures.

The content of promoter is between 0.005 and 500%, preferably between 0.005 and 100%, by weight of the weight of the noble metal or metals. The deposition of the promoter on the catalytic support is advantageously carried out by impregnation.

A preferred catalyst comprises one or more noble metals chosen from palladium, platinum and their mixtures, which are activated by bismuth and/or lead supported on active charcoal or graphite.

The catalyst is prepared by impregnation for a time varying from at least a few seconds to a few hours, generally of between 15 minutes and 2 hours, while keeping stirred the mixture of catalyst support and the solution comprising the noble metals. The catalyst based on noble metals is subsequently dried and then impregnated with the solution of the promoter. This operation precedes the stage of reducing the catalyst, which is carried out at a temperature of between 20 and 400° C. using chemical reducing agents of the following types: formaldehyde, sodium formate, sodium borohydride, hydrogen, hypophosphorous acid, hydrazine, glucose or other reducing sugars.

An alternative for the preparation of the catalyst is to carry out a first impregnation with the promoter, followed by a second stage of impregnation with the noble metal or metals. The catalyst is subsequently reduced.

Another alternative for the preparation of the catalyst is to carry out a single impregnation with a noble metal or metals and with a promoter. The catalyst is subsequently reduced.

The details of the procedure for the oxidation stage according to the present invention are set out below and will be illustrated in the examples:

an aqueous solution of the diol (II), the concentration of diol (II) preferably being between 1 and 70% by weight, is introduced into a reactor equipped with a stirring device. The lower limit of the diol concentration is dictated by concern for the profitability of the process and its upper limit takes into account the solubility of oxygen in the media under consideration and the risk of crystallization of the salt of the acid (III) formed during the reaction;

an amount of a supported and activated catalyst as described above is dispersed in this solution;

the oxidation reaction is initiated by simultaneously starting to flush with a gas comprising oxygen, such as air. The pH of the medium is regulated by the addition of an alkaline agent, the reaction temperature generally lying between 10° C. and 95° C., preferably between 20 and 95° C., and even between 25° C. and 70° C., for a reaction time of between 20 minutes and 15 hours.

The alkaline agent used is advantageously chosen from calcium hydroxide, sodium hydroxide, potassium hydroxide, lithium hydroxide, magnesium hydroxide, ammonia, sodium carbonate, zinc carbonate, manganese carbonate and their mixtures, according to the purpose desired. It is also conceivable to use zinc or manganese carbonate or any other zinc or manganese salt for which the corresponding hydroxides are obtained in situ by addition of an alkaline agent, such as sodium hydroxide or potassium hydroxide. The alkaline agent is also intended to neutralize the acid (III) produced, in order to maintain a constant catalytic activity. The alkaline agent has in fact to maintain the pH at a value sufficient to ensure the desorption of the acid (III) formed. This precaution makes it possible in addition to avoid the formation of undesirable byproducts, for example resulting from excessive oxidation of the diol.

In practice, the pH is maintained at a value of between 4 and 11, preferably between 5.5 and 7.5. The process according to the invention makes it possible to achieve highly advantageous selectivities exceeding 90%. These performances are not detrimentally affected by a high recycling and/or reactivation number for the oxidation catalyst employed in accordance with the present invention. This is because the catalysts employed have an appreciable lifetime and are easily regenerated in situ by deposition of a fresh charge of promoter or by in situ reduction of the deactivated catalyst.

This first oxidation stage is advantageously carried out in an aqueous solvent. An organic solvent or a mixture of organic solvents can also be employed. An aqueous/organic medium may also prove to be beneficial. The organic solvent constituting the medium in which the reaction for oxidation of the diol (II) is carried out is chosen from any at least partial solvent of the said diol (II) which is inert under the operating conditions. The solvents are chosen from aliphatic, cycloaliphatic or aromatic hydrocarbons; alkyl or alkenyl esters of aliphatic carboxylic acids; aliphatic, aromatic or cyclic ethers; aliphatic, cycloaliphatic or aromatic nitriles; or aliphatic, cycloaliphatic or aromatic ketones. Mention may be made, as nonlimiting examples, of:

hydrocarbons, such as n-hexane, n-heptane, n-octane, n-nonane, benzene, styrene, ethylbenzene, toluene, meta-xylene, isopropylbenzene, cyclohexane or 4-methylpent-2-ene;

esters, such as ethyl formate, butyl formate, isobutyl formate, ethyl acetate, allyl acetate, propyl acetate, butyl acetate, hexyl acetate, ethyl propionate, vinyl propionate, ethyl acrylate, butyl butyrate, methyl isobutyrate or methyl butyrate;

ethers, such as cis-1-ethoxybut-1-ene, trans-1-ethoxybut-1-ene, dibutyl ether, 1-isopropoxybutane, 1,1-dimethoxyethane, 1,1-diethoxyethane, 1,1-dimethoxypropane, 1-ethoxybutane, diisopropyl ether, 1-ethoxyhexane, 2-ethoxypropane, 1-methoxybuta-1,3-diene, butyl vinyl ether, furan or 2,5-dimethylfuran;

nitriles, such as butyronitrile, acetonitrile, acrylonitrile, propionitrile or tetrahydrobenzonitrile;

ketones, such as cyclopentanone, dipropyl ketone, heptanone, methyl isopropyl ketone, 5-methylhexan-2-one, 2-pentanone or 4-methylpent-3-en-2-one.

The oxygen used to initiate the oxidation reaction can be molecular oxygen, air, air enriched or depleted in oxygen, or any other mixture of oxygen with an inert gas.

The total pressure under which the reaction is carried out can be greater than, equal to or less than atmospheric pressure; it is generally between 0.5 and 5 bar. The oxygen partial pressure is preferably between 0.05 bar and 2 bar. The oxidation of the diol (II) to give the α-keto acid (III) can be carried out either by maintaining a constant pressure, or by circulating the oxygen or the gas comprising it in the device in which the reaction is carried out, or by sparging the oxygen or the gas comprising it into the reaction mixture.

The equipment in which the process according to the invention is carried out may, of course, not be specific to the said process.

2) Condensation Stage (ii):

According to this stage, one mole of methyl mercaptan (MeSH), in its gaseous or liquid form, and one mole of the α-keto acid (III) prepared above are condensed according to the reaction scheme (ii):

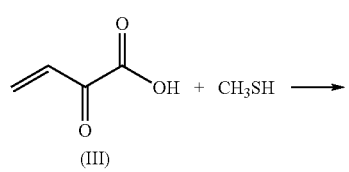

(III)

-continued

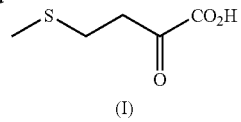

(I)

The field of the present invention is that of the manufacture of the acid (I) as final product or intermediate product. The reactivity of thiols is in many respects similar to that of alcohols. They can, depending on the catalytic conditions employed, add to α,β-unsaturated aldehydes, α,β-unsaturated ketones and α,β-unsaturated acids in the 1,2-position, resulting in the monohemithioacetal, or in the 1,4-position, resulting in the 3-alkylthio-propionaldehyde. By structural analogy, the acid (III) comes fully within the category of activated olefins.

Two catalytic routes are conventionally recommended for selectively and efficiently adding thiols to α,β-unsaturated carbonyl derivatives in the 4-position. The first is an ionic addition catalysed by bases. The second is a radical addition initiated by azo or peroxide compounds. However, this method of initiation generally results in usually undesirable polymers.

The prior art gives details of various catalysts which make it possible to direct the regioselectivity of the addition in the 1,2- or 1,4-fashion. Nevertheless, the 1,4-addition of Michael type of thiols to α,β-unsaturated ketones remains the commonest.

The crude starting material comprising the salified or unsalified acid (III) is optionally subjected to a first treatment which makes it possible to remove the impurities coproduced during the oxidation of the diol (II). This crude product can also be subjected to degassing. The excess diol (II) corresponding to the diol which has not reacted can advantageously be recycled to the oxidation stage, for example by distillation or extraction. The aqueous solution of the acid (III) can optionally be concentrated prior to being brought into contact with gaseous or liquid methyl mercaptan. This aqueous solution of the acid (III) is subsequently brought into contact with gaseous or liquid methyl mercaptan in order to result in the acid (I).

This stage can optionally be carried out in the presence of a basic catalyst or of a mixture of basic catalysts. Appropriate basic catalysts are, for example, aliphatic amines, such as methylamine, ethylamine, propylamine, butylamine, pentylamine, hexylamine, heptylamine, octylamine or isopropylamine; aromatic amines, such as aniline, benzylamine or pyridine; hexamethylenetetramine, triethylamine, diisopropylethylamine, diazabicylo-[2.2.2]octane, N,N-dimethylbenzylamine, N-methyldiphenylamine, N-ethyl-3,3'-diphenyldipropylamine or an N-alkylmorpholine, such as N-methyl-morpholine, or triton B, these amines optionally being combined with an organic or inorganic acid; the latter is preferably chosen from formic acid, acetic acid, propanoic acid and butanoic acid, phosphoric acid and sulphuric acid.

The addition of methyl mercaptan to the α-keto acid (III) is advantageously acid/base catalysed, for example using a catalyst consisting of a combination of an organic or inorganic acid and an organic or inorganic base. Acetic acid is preferably used.

On the industrial scale, liquid or gaseous methyl mercaptan is conveyed into a reactor comprising the aqueous solution, concentrated or not concentrated and degassed or not degassed beforehand, of the acid (III).

The condensation between the acid (III) and methyl mercaptan can be carried out batchwise or continuously. The acid (III) and methyl mercaptan are introduced simultaneously or alternatively, while observing the stoichiometric ratio. However, it is possible to envisage operating with a deficiency or excess of methyl mercaptan, depending on the reaction pursued.

The reaction can be carried out by continuous introduction between the aqueous solution of the acid (III) and gaseous methyl mercaptan into a gas/liquid reactor. In this case, the methyl mercaptan can be added cocurrentwise or countercurrentwise. Alternatively, the reaction can be carried out by continuous introduction of the aqueous solution of the acid (III) and of liquid methyl mercaptan into a batch or plug-flow reactor. The reaction temperature should not exceed 80° C.

The catalysts for condensation between the acid (III) and methyl mercaptan are generally chosen according to several criteria:
- the conversion and yield of acid (I);
- the reaction kinetics;
- the selectivity and tendency to coproduce undesirable impurities, which are usually high molecular weight entities resulting from side polymerizations during the synthesis but also during the storage of the desired product;
- the property of stabilizing the product during its prolonged storage.

The equipment in which the process according to the invention is carried out is not specific to the said process.

The purpose of the following examples is to illustrate the invention without limiting the scope thereof. Examples 1-7 illustrate the synthesis of compounds of the invention and Examples 8 and 9 illustrate the nutritional advantage of compounds of the invention, in support of the FIGURE which represents the value of effectiveness of dl-methionine and of KMB as a function of the application dose in the trials of Example 9.

EXAMPLE 1

Preparation of a Catalyst (A)

1% Bi/5% Pt on Alumina 100 grams of γ-alumina beads are prepared, according to the process disclosed in French Patent Application FR-A-1 449 904, by autoclaving active alumina agglomerates in the presence of acid and then drying and calcining. These beads exhibit a specific surface of 100 m²/g and a total pore volume of 0.90 cm³/g composed of macropores having a diameter of greater than 100 nm.

These beads are subsequently impregnated with 90 cm³ of a bismuth nitrate solution comprising 1 gram of bismuth.

After being in contact for 30 minutes, the beads are dried at 150° C. and then calcined under air at 600° C. for 3 hours.

They are subsequently impregnated with 90 cm³ of a chloroplatinic acid solution comprising 5 grams of platinum.

After being in contact for 30 minutes, the beads are dried at 150° C. and then activated for 3 hours at 300° C. in a stream of hydrogen moving at 200 litres per hour.

The catalyst (A) thus prepared comprises, by weight with respect to the alumina support, 5% of platinum and 1% of bismuth.

EXAMPLE 2

Preparation of a Catalyst (B)

5% Bi/5% Pt on Active Charcoal 100 grams of active charcoal sold by Ceca under the name Ceca 3S are washed successively with a hydrochloric acid solution and then with deionized water to remove the soluble impurities. The support is subsequently dried in an oven at 120° C. for 24 hours.

These pellets are subsequently impregnated with a bismuth nitrate solution comprising 5 g of bismuth.

After being in contact for 4 hours, the pellets are dried at 120° C. for 24 hours.

They are subsequently impregnated with a chloroplatinic acid solution comprising 5 grams of platinum.

After being in contact for 4 hours, the pellets are dried at 120° C. and then activated for 3 hours at 300° C. in a stream of hydrogen moving at 200 litres per hour.

The catalyst (B) thus prepared comprises, by weight with respect to the active charcoal support, 5% of platinum and 5% of bismuth.

EXAMPLE 3

Preparation of a Catalyst (C)

5% Pt/5% Bi on Active Charcoal 100 grams of active charcoal sold by Ceca under the name Ceca 3S are washed successively with a hydrochloric acid solution and then with deionized water to remove the soluble impurities. The support is subsequently dried in an oven at 120° C. for 24 hours.

These pellets are subsequently impregnated with a hexachloroplatinic acid solution comprising 5 g of platinum.

After being in contact for 4 hours, the pellets are dried at 120° C. for 24 hours.

They are subsequently impregnated with a bismuth nitrate solution comprising 5 grams of bismuth.

After being in contact for 4 hours, the pellets are dried at 120° C. and then activated for 3 hours at 300° C. in a stream of hydrogen moving at 200 litres per hour.

The catalyst (C) thus prepared comprises, by weight with respect to the active charcoal support, 5% of bismuth and 5% of platinum.

EXAMPLE 4

Preparation of a Catalyst (D)

5% Bi/4% Pd/1% Pt on Active Charcoal 100 grams of active charcoal sold by Ceca under the name Ceca 3S are washed successively with a hydrochloric acid solution and then with deionized water to remove the soluble impurities. The support is subsequently dried in an oven at 120° C. for 24 hours.

These pellets are subsequently impregnated with a bismuth nitrate solution comprising 5 g of bismuth.

After being in contact for 4 hours, the pellets are dried at 120° C. for 24 hours.

They are subsequently impregnated with a palladium nitrate and chloroplatinic acid solution comprising 4 grams of palladium and 1 gram of platinum.

After being in contact for 4 hours, the pellets are dried at 120° C. and then activated for 3 hours at 300° C. in a stream of hydrogen moving at 200 litres per hour.

The catalyst (D) thus prepared comprises, by weight with respect to the active charcoal support, 4% of palladium, 1% of platinum and 5% of bismuth.

EXAMPLE 5

Preparation of a Catalyst (E) 1% Bi/5% Pt on Graphite Carbon 100 grams of graphite carbon sold by SN2A under the name Y 200 (acetylene black) are used as is to synthesize the catalyst (E). The support is dried beforehand in an oven at 120° C. for 24 hours.

This powdered support is subsequently impregnated with a bismuth nitrate solution comprising 1 g of bismuth.

After being in contact for 4 hours, the impregnated support is dried at 120° C. for 24 hours.

The powdered catalyst is subsequently impregnated with a chloroplatinic acid solution comprising 5 grams of platinum.

After being in contact for 4 hours, the catalyst is dried at 120° C. and then activated for 3 hours at 300° C. in a stream of hydrogen moving at 20 litres per hour.

The catalyst (E) thus prepared comprises, by weight with respect to the graphite support, 5% of platinum and 1% of bismuth.

EXAMPLE 6

Oxidation of but-3-ene-1,2-diol (II) to Give 2-oxobut-3-enoic Acid (III) in the Presence of the Catalyst (D)

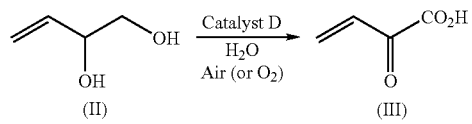

Aqueous solutions comprising 0.1 to 50% w/w of but-3-ene-1,2-diol (II) are oxidized in a fully stirred jacketed glass reactor with a capacity of 500 ml. The air is introduced into the reaction medium via a dip pipe optionally equipped with a sintered glass. The pH is regulated by controlled addition of dilute sodium hydroxide using a pump controlled by a pH meter. The pH, the sodium hydroxide consumption, the temperature (50° C.) and the oxygen partial pressure in the gaseous head space (using an oximeter) are continuously recorded.

Samples of the reaction medium are regularly withdrawn and the reaction products are analysed by high pressure liquid chromatography (HPLC) and gas chromatography (GC).

The catalyst, reduced beforehand, and the water are introduced into the reactor and the suspension is heated, with stirring, to the desired reaction temperature under a stream of nitrogen, so as to drive off the dissolved oxygen. The but-3-ene-1,2-diol (II) is introduced and, at time zero, the nitrogen is replaced with air, the pH is adjusted to the desired value and the oxidation is begun.

The degree of conversion of the but-3-ene-1,2-diol is defined as the percentage of but-3-ene-1,2-diol consumed. The yield of a product is the percentage of but-3-ene-1,2-diol converted into this product. The reaction kinetics can be monitored by the:

disappearance of the but-3-ene-1,2-diol (II), amount of sodium hydroxide necessary to keep the pH constant due to the formation of the acid (III).

This example is carried out in the presence of the catalyst (D) obtained in Example 4, the operation being carried out for a time of 12 hours in an atmosphere depleted and controlled with regard to oxygen.

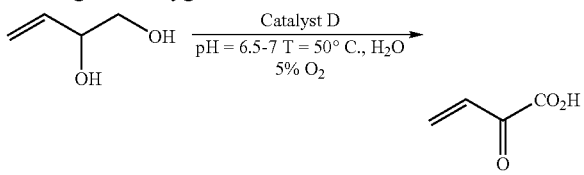

The following are charged to a 500 ml jacketed reactor rendered inert beforehand with nitrogen and equipped with a mechanical stirrer, a temperature probe and a pH probe:

Weight of catalyst introduced: 0.302 g

| Reactants | Purity | Molar mass (g/mol) | Weight introduced (g) | Number of moles | Number of equivalents |
|---|---|---|---|---|---|
| 3-Butene-1,2-diol | 99% | 88.11 | 4.1093 | 0.05 | 1.00 |
| Water | 100% | 18 | 300 | 16.67 | 361 |

The reaction medium is brought to 50° C. The air flow rate is set at 2.6 l/h and the nitrogen flow rate is set at 8 l/h. The % $O_2$, measured via an oximeter, displays approximately 5 vol %. The stirring rate is set at 300 revolutions/min. The pH of the reaction medium is regulated in the range 6-7 by addition of dilute aqueous sodium hydroxide (0.15% w/w). The rate of disappearance of the but-3-ene-1,2-diol is measured by gas chromatography. The appearance of the α-keto acid (III) is determined by high pressure liquid chromatography. The results are:

Degree of conversion (diol II)=38% after 6 hours

Degree of conversion (diol II)=64% after 12 hours

EXAMPLE 7

Oxidation of but-3-ene-1,2-diol (II) to 2-oxo-but-3-enoic Acid (III) in the Presence of the Catalyst (D)

This example is carried out in the presence of the catalyst (D) obtained in Example 4, the reaction being carried for a period of 4 hours in the presence of air at pH=7.5.

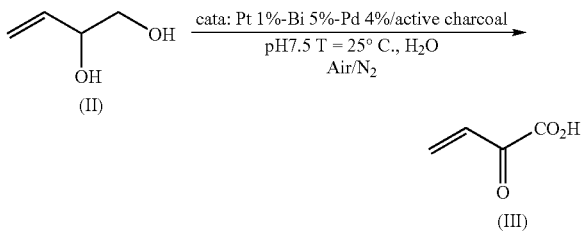

The following are charged to a 100 ml jacketed reactor rendered inert beforehand with nitrogen and equipped with a mechanical stirrer, a temperature probe and a pH probe:

| | |
|---|---|
| Catalyst (D): | 0.5 g |
| Diol (II): | 0.5 g |

The reaction medium is maintained at 30° C. The air flow rate is set at 12 l/h and the nitrogen flow rate is set at 9 l/h. The stirring rate is set at 1300 revolutions/min. The pH of the reaction medium is regulated at 7.5 by addition of dilute aqueous sodium hydroxide (0.5% w/w). The rate of disappearance of but-3-ene-1,2-diol (II) is measured by gas chromatography. The appearance of the 2-oxo-but-3-enoic acid (III) is determined by high pressure liquid chromatography.

The performance levels measured are:
Degree of conversion (diol II)=75% after 1 h
Degree of conversion (diol II)>99% after 4.5 h
Yield of 2-oxo-but-3-enoic acid (III)>85%

EXAMPLE 8

Illustration of the Nutritional Value of 2-oxo-4-methylthiobutyric Acid (KMB) in the Chicken, as a Source of Methionine 8.1) Experimental Principle:
A "dose-response" experimental model was used.
The starting material is a food base that is deficient in methionine, methionine being the nutritional element for which it is desired to observe a response, and then the said nutritional element that is lacking is introduced in the form of 2-hydroxy-4-methylthiobutyric acid (product produced by the applicant under the name Rhodimet™ AT88) according to system R2 and in the form of 2-oxo-4-methylthiobutyric acid (KMB) according to system R3, at the same doses, and then the performance levels obtained in each of the systems are compared, system R1 corresponding to no introduction of methionine.

8.2) Experimental Scheme:

4 chickens per cage are tested.

Three treatments R1 (without added methionine), R2 (+Rhodimet™ AT88) and R3 (+KMB) were carried out, and were each repeated nine times, according to Table 1 below.

TABLE 1

| | Food base over 0-7 days 0.45% total Met Food base over 7-21 days Maize soya growth 0.32% total Met | | |
|---|---|---|---|
| System | R1 | R2 | R3 |
| Item | — | Rhodimet ™ AT88 | KMB |
| Dose item (%) | — | 0.09 | 0.09 |
| Numbers | 36 | 36 | 36 |

Table 2 below gives the results obtained over the period of 7-21 days.

TABLE 2

| | | R1 | R2 | R3 |
|---|---|---|---|---|
| Systems | | | | |
| Item | | — | Rhodimet ™ AT88 | KMB |
| Dose Met (%) | | 0 | 0.09 | 0.09 |
| Weight indiv D7 (g) | Means | 134.8 | 135.1 | 134.9 |
| | Standard deviation | 1.85 | 0.93 | 1.82 |
| | CV | 1.37 | 0.69 | 1.35 |
| | Number of animals | 36 | 36 | 36 |
| Weight indiv D21 (g) | Means | 641 a | 744 b | 730 b |
| | Standard deviation | 56.6 | 28.0 | 28.5 |
| | CV | 8.84 | 3.76 | 3.90 |
| | Number of animals | 36 | 36 | 36 |
| | Delta (%) | | 16.1 | 14.0 |
| Weight gain D7-D21 (g) | Means | 506 a | 609 b | 596 b |
| | Standard deviation | 55.8 | 27.9 | 27.1 |
| | CV | 11.02 | 4.58 | 4.54 |
| | Delta (%) | | 20.4 | 17.7 |
| Ingested D7-D21 (g) | Means | 971 a | 1036 b | 1044 b |
| | Standard deviation | 80.3 | 40.3 | 68.2 |
| | CV | 8.27 | 3.89 | 6.54 |
| | Delta (%) | | 6.7 | 7.5 |
| Consumption index D7-D21 (g/g) | Means | 1.930 a | 1.702 b | 1.752 b |
| | Standard deviation | 0.1633 | 0.0423 | 0.0836 |
| | CV | 8.46 | 2.49 | 4.77 |
| | Delta (%) | | −11.8 | −9.2 |

NB: The values given a letter a or b are significantly different from the threshold of 5%

The consumption index over a given period is the ratio of food ingested to weight gain, over this same period, which corresponds to the amount of food required to obtain a weight gain of 1 kg.

The introduction of methionine in the form of KMB (R3) allows an improvement in the weight gain over the period of approximately 90 g and a decrease in the consumption index of 9%, which are not significantly different from those obtained with the hydroxy analogue of methionine (Rhodimet™ AT88, R2).

KMB therefore has a nutritional value equivalent to that of the hydroxy analogue of methionine.

EXAMPLE 9

Another Illustration of the Nutritional Value of 2-oxo-4-methylthiobutyric Acid (KMB) in a Chicken as a Source of Methionine 9.1) Experimental Principle:

The starting product is a food base that is deficient in methionine, methionine being the nutritional element for which it is desired to observe a response, and the said nutritional element that is lacking is then introduced in the reference forms and in the test form, and then the performance levels obtained in each of the systems are compared, system R1 corresponding to no introduction of methionine.

Two chickens per cage are tested, with controlled randomization by chance.

Seven treatments were carried out:

R1: without added methionine,

R2 and R3: +Rhodimet™ NP99 (D,L-methionine powder sold by the applicant) at two different doses, R4 and R5: +Rhodimet™ AT88, at two different doses R6 and R7: +KMB, at two different doses.

They were each repeated 14 times and are represented in Table 3 below.

The results obtained are given in Table 4. The results obtained

TABLE 3

| | Feed base 0-7 days Maize soya starter (50% NP99 and 50% AT88, for an equivalent of 0.22% of Met added) Feed base 7-21 days Maize soya growth | | | | | | |
|---|---|---|---|---|---|---|---|
| Systems | R1 | R2 | R3 | R4 | R5 | R6 | R7 |
| Item | — | NP 99 | NP 99 | AT88 | AT88 | KMB | KMB |
| Doses item (%) | — | 0.100 | 0.200 | 0.113 | 0.225 | 0.102 | 0.204 |
| Weight of meal foodstuff to be treated (kg) | 50 | 50 | 50 | 50 | 50 | 50 | 50 |
| Weight of experimental foodstuff granules (kg) | 40 | 40 | 40 | 40 | 40 | 40 | 40 |
| Numbers in the experiment | 28 | 28 | 28 | 28 | 28 | 28 | 28 | show that addition of 0.1% of methionine in the form of NP99 makes it possible to significantly increase the weight gain (+90 g) and to significantly decrease the consumption index (−11%). The absence of effect of the supplementation dose suggests that the methionine needs were covered from the dose of 0.1%.

The results obtained with the addition of AT88 or KMB are similar and not significantly different from those obtained with DL-methionine (NP99). KMB therefore, like AT88, has a nutritional value equivalent to that of DL-methionine.

TABLE 4

| | Systems | R1 | R2 | R3 | R4 | R5 | R6 | R7 |
|---|---|---|---|---|---|---|---|---|
| | Item | Control | NP99 | NP99 | AT88 | AT88 | KMB | KMB |
| | Dose | / | 0.100% | 0.200% | 0.113% | 0.225% | 0.102% | 0.204% |
| Mortality | D7-D21 | 3.6% | 0.0% | 0.0% | 0.0% | 0.0% | 7.1% | 0.0% |
| Weight gain D7-D21 (g) | Means | 454 a | 544 b | 527 b | 549 b | 559 b | 563 b | 535 b |
| | Standard deviation | 56.4 | 73.3 | 78.6 | 51.2 | 49.0 | 57.4 | 44.0 |
| | CV | 12.42 | 13.48 | 14.90 | 9.31 | 8.76 | 10.18 | 8.23 |
| | Delta (%) | | 19.8 | 16.2 | 21.0 | 23.2 | 24.1 | 17.9 |
| Consumption D7-D21 (g) | Means | 780 | 832 | 823 | 850 | 846 | 864 | 819 |
| | Standard deviation | 98.9 | 113.5 | 116.5 | 64.9 | 65.2 | 65.4 | 67.6 |
| | CV | 12.67 | 13.64 | 14.15 | 7.64 | 7.70 | 7.58 | 8.25 |
| | Delta (%) | | 6.7 | 5.5 | 9.0 | 8.4 | 10.7 | 5.0 |

TABLE 4-continued

| Systems Item Dose | R1 Control / | R2 NP99 0.100% | R3 NP99 0.200% | R4 AT88 0.113% | R5 AT88 0.225% | R6 KMB 0.102% | R7 KMB 0.204% |
|---|---|---|---|---|---|---|---|
| Cl D7-D21 Means | 1.722 a | 1.531 b | 1.564 b | 1.552 b | 1.514 b | 1.539 b | 1.533 b |
| Standard deviation | 0.1271 | 0.0562 | 0.0653 | 0.0829 | 0.0653 | 0.0895 | 0.0731 |
| CV | 7.38 | 3.67 | 4.18 | 5.34 | 4.31 | 5.81 | 4.77 |
| Number of values | 13 | 14 | 14 | 14 | 14 | 12 | 14 |
| Delta (%) | | −11.1 | −9.2 | −9.9 | −12.1 | −10.6 | −11.0 |

Zootechnical performance levels as a function of treatments (period 7-21 days)

Biological value of KMB:

The results obtained according to Table 4 also make it possible to calculate an "approximate" biological value for KMB. Since the dose-response curve is based only on two points, this value cannot be considered to be definitive, but makes it possible to have a more quantitative approach with regard to the biological value of KMB without prejudging its value for use.

To compare the two products, the efficiency of methionine conversion is calculated, which consists in determining the mean amount of active material (methionine or KMB in mg) required to obtain the additional grams of weight gain relative to the weight gain with the control having the deficiency. The smaller the number of grams required to obtain one gram of weight gain, the greater the efficiency of the product, as illustrated in the FIGURE.

The ratio of KMB efficiency to DL-methionine efficiency is then calculated by calculating the ratio of the conversion efficiency values calculated at the two doses used. Thus, the relative efficiency values show that KMB exhibits better efficiency than DL-methionine, respectively 118.5 and 111.5% for the doses 0.1 and 0.2%.

In conclusion, Examples 8 and 9 demonstrate that KMB introduced into the food is assimilated by the animal in the intestines and that it is used as a source of methionine in a manner at least equivalent to DL-methionine for growth.

BRIEF DESCRIPTION OF FIGS

The sole FIGURE in this application depicts conversion effectiveness values for DL-methionine and KMB

The invention claimed is:

1. Process for preparing 2-oxo-4-methylthiobutyric acid and its salts, the said acid corresponding to the formula (I)

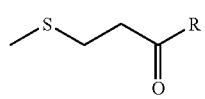

in which R represents a carboxyl group, and its salts, the said process comprising the following stages:

but-3-ene-1,2-diol (II) is catalytically and selectively oxidized to give 2-oxobut-3-enoic acid (III), according to the following reaction scheme (i):

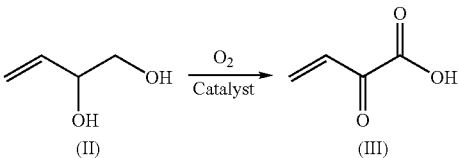

and methyl mercaptan is selectively condensed with 2-oxobut-3-enoic acid (III), according to the following reaction scheme (ii):

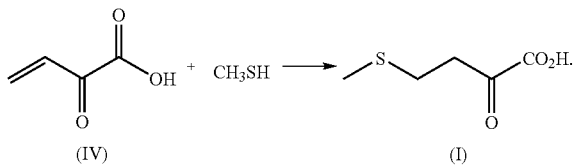

2. Process for preparing a compound corresponding to the formula

in which R represents a group chosen from COOR', CONH$_2$, CONHR' or CONR'R", where R' and R" are chosen, independently of one another, from the group of linear or branched alkyl radicals having from 1 to 12 carbon atoms and cycloalkyl radicals having from 3 to 12 carbon atoms, wherein 2-oxo-4-methylthiobutyric acid (I) is obtained according to the process defined in claim 1 and then an esterification or amidation stage is carried out.

3. Process according to claim 1, wherein the catalyst comprises at least one noble metal chosen from palladium, platinum, ruthenium, iridium, rhodium and their mixtures.

4. Process according to claim 3, wherein the catalyst comprises at least one promoter chosen from bismuth, lead, antimony, tin, niobium, tellurium, indium, gallium, zinc, copper, nickel, cobalt, gold, silver, tungsten, molybdenum, rhenium, vanadium, chromium, manganese, iron and their mixtures.

5. Process according to claim 3, wherein the catalyst comprises an inert support chosen from alumina, silica, active charcoals, graphite, titanium oxide, zirconia, silicon carbide, mixed oxides based on zirconium and on cerium, or acetylene black.

6. Process according to claim 4, wherein the promoter is deposited on the support by impregnation.

7. Process according to claim 3, wherein the catalyst comprises a noble metal chosen from palladium, platinum and their mixtures, a promoter chosen from bismuth and lead and their mixtures and a support chosen from active charcoal AND graphite.

8. Process according to claim 3, wherein the content of the noble metal or metals is between 0.1 and 10% by weight with respect to the catalytic support.

9. Process according to claim 4, wherein the content of the promoter is between 0.005 and 500% by weight of the weight of the noble metal or metals.

10. Process according to claim 4, wherein the content of the promoter can reach 10% by weight of the weight of the catalyst.

11. Process according to claim 3, wherein the oxidation is carried out in a neutral or alkaline medium, at a pH maintained between 4 and 11.

12. Process according to claim 11, wherein an alkaline agent chosen from calcium hydroxide, sodium hydroxide, potassium hydroxide, lithium hydroxide, magnesium hydroxide, ammonia, sodium carbonate, zinc carbonate, manganese carbonate and their mixtures is added.

13. Process according to claim 1, wherein the oxidation is initiated by starting to flush with a gas comprising oxygen, such as air.

14. Process according to claim 1, wherein the oxidation is carried out at a temperature of between 10 and 95° C.

15. Process according to claim 1, wherein the oxidation takes place over a period of between 20 minutes and 15 hours.

16. Process according to claim 1, wherein, in order to condense methyl mercaptan with 2-oxobut-3-enoic acid, methyl mercaptan is used in the gaseous form or in the liquid form.

17. Process according to claim 16, wherein the condensation is carried out in the presence of a basic catalyst.

18. Process according to claim 17, wherein the catalyst is chosen from aliphatic amines, such as methylamine, ethylamine, propylamine, butylamine, pentylamine, hexylamine, heptylamine and octylamine, aromatic amines, such as aniline or pyridine, hexamethylenetetramine, triethylamine, diisopropylethylamine, diazabicylo-[2.2.2]octane, N,N-dimethylbenzylamine, N-methyldiphenylamine, N-ethyl-3,3'-diphenyldipropylamine or an N-alkylmorpholine, such as N-methylmorpholine, or triton B.

19. Process according to claim 18, wherein the catalyst is an N-alkylmorpholine, such as N-methylmorpholine, combined with an organic acid chosen from formic acid, acetic acid, propanoic acid and butanoic acid.

20. Process for preparing 2-oxobut-3-enoic acid (III), wherein but-3-ene-1,2-diol (II) is catalytically and selectively oxidized according to claim 1.

* * * * *